(12) United States Patent
De Maria et al.

(10) Patent No.: US 7,994,125 B2
(45) Date of Patent: Aug. 9, 2011

(54) STEM CELL FACTOR FOR PREVENTING CHEMOTHERAPY-INDUCED DEPLETION OF BLOOD CELLS

(75) Inventors: Ruggero Marchiano De Maria, Rome (IT); Ann Pegna Zeuner, Rome (IT)

(73) Assignee: Istituto Superiore Di Sanita, Rome (IT)

(*) Notice: Subject to any disclaimer, the term of this patent is extended or adjusted under 35 U.S.C. 154(b) by 0 days.

(21) Appl. No.: 10/487,075

(22) PCT Filed: Feb. 14, 2003

(86) PCT No.: PCT/IB03/00930
§ 371 (c)(1),
(2), (4) Date: Apr. 7, 2005

(87) PCT Pub. No.: WO2004/071523
PCT Pub. Date: Aug. 26, 2004

(65) Prior Publication Data
US 2005/0181990 A1    Aug. 18, 2005

(51) Int. Cl.
*A61K 38/00* (2006.01)
*A61K 38/18* (2006.01)
(52) U.S. Cl. ............... 514/7.9; 514/2; 514/7.6; 514/7.7; 514/7.8
(58) Field of Classification Search .................. None
See application file for complete search history.

(56) References Cited

U.S. PATENT DOCUMENTS

| | | | |
|---|---|---|---|
| 5,620,685 A | 4/1997 | Nishi et al. | |
| 2004/0092445 A1* | 5/2004 | Heuer et al. | 514/12 |

FOREIGN PATENT DOCUMENTS

| | | | |
|---|---|---|---|
| EP | 0 423 980 A | 4/1991 | |
| WO | 92/00376 A | 1/1992 | |

OTHER PUBLICATIONS

Pietsch et al. Effects of human stem cell factor (c-kit ligand) on proliferation of myeloid leukemia cells: heterogeneity in response and synergy with other hematopoietic growth factors. 1992. Blood. Sep. 1;80(5):1199-1206.*
Zeuner et al. Stem cell factor protects erythroid precursor cells from chemotherapeutic agents via up-regulation of BCL-2 family proteins. Blood. Jul. 1, 2003;102(1):87-93. Epub Mar. 13, 2003.*
Sattler M, Salgia R.Targeting c-Kit mutations: basic science to novel therapies. 2004. Leuk Res. May;28 Suppl 1:S11-20.*
Basser et al. J Clin Oncol 1998;16:1899-1908.*
Smith et al. Acta Hematol 2001;105:143-50.*
Fanning et al. Gynecol Oncol 2000;79:97-100.*
Facon et al. Blood 1999;94:1218-25.*
Weaver et al. Blood 1996;88:3323-8.*
Tong et al. Blood 1993;82:784-91.*
Liebmann et al; "Protection From Lethal Irradiation by the Combination of Stem Cell Factor and Tempol"; Radiation Research, 1994, vol. 137, No. 3, pp. 400-404, XP009018564.
Liebmann et al; "Nitric Oxide Modulation Enhances the In Vivo Protection From Lethal Irradiation by Stem Cell Factor"; Radiation Oncology Investigations, 1995, vol. 2, No. 6, pp. 264-268, XP009018562.
Facon et al; "Stem Cell Factor in Combination With Filgrastim After Chemotherapy Improves Peripheral Blood Progenitor Cell Yield and Reduces Apheresis Requirements in Multiple Myeloma Patients: A Randomized, Controlled Trial"; Blood, Aug. 15, 1999, vol. 94, No. 4, pp. 1218-1225, XP002256691.
The Third European Workshop on Cell Death, Feb. 23-28, 2002, Abstract at Workshop, Zeuner et al; "Stem Cell Factor Upregulates BCL-2 Family Members and Protects Erythroid Precursor Cells From Chemotherapy-Induced Apoptosis", Instituto di Patologia Generale, Universita' di Catania, Italy and Department of Hematology and Oncology, Instituto Superiore di Sanita', Rome, Italy.
Inteniational Search Report of PCT/IB03/00930, Oct. 6, 2003.
Arcasoy et al. "Erythropoietin and erythropoietin receptor expression in head and neck cancer: Relationship to tumor hypoxia" Clin. Cancer Res. 20:20-27 (2005).
Blaise et al. "Rescue of haemopoiesis by a combination of growth factors including stem-cell factor" The Lancet 356:1325-1326 (2000).
Dagnon et al. "Expression of erythropoietin and erythropoietin receptor in non-small cell lung carcinomas" Clin. Cancer Res. 11:993-999 (2005).
Eramo et al. "Chemotherapy resistance of glioblastoma stem cells" Cell Death and Differ. 13:1238-1241 (2006).
Food and Drug Administration, Center for Biologics Evaluation and Research, 24th Meeting of the Biological Response Modifiers Advisory Committee.
Haseyama et al. "Stem cell factor protects c-kit human primary erythroid cells from apoptosis" Exp. Hematol. 29:833-841 (2001).
Hassan et al. "Stem cell factor as a survival and growth factor in human normal and malignant hematopoiesis" Acta Haematol. 95:257-262 (1996).
http://.medsafe.govt.nz/profs/datasheet/s/stemgeninj.htm.
Ikeda et al. "Expression and functional role of the proto-oncogene c-kit in acute myeloblastic leukemia cells" Blood 78:2962-2968 (1991).
Nishio et al. "Stem cell factor prevents fas-mediated apoptosis of human erythroid precursor cells with Src-family kinase dependency" Exper. Hematol. 29:19-29 (2001).
Pidhorecky et al. "Gastrointestinal stromal tumors: Current diagnosis, biologic behavior, and management" Annals of Surgical Oncol. 7:705-712 (2000).

(Continued)

*Primary Examiner* — Q. Janice Li
(74) *Attorney, Agent, or Firm* — Browdy and Neimark, PLLC

(57) ABSTRACT

The present invention relates to the use of Stem Cell Factor in the protection of multiprogenitor cells and in the prevention of chemotherapy-induced depletion of blood cells.

12 Claims, 6 Drawing Sheets

OTHER PUBLICATIONS

Figure 1:
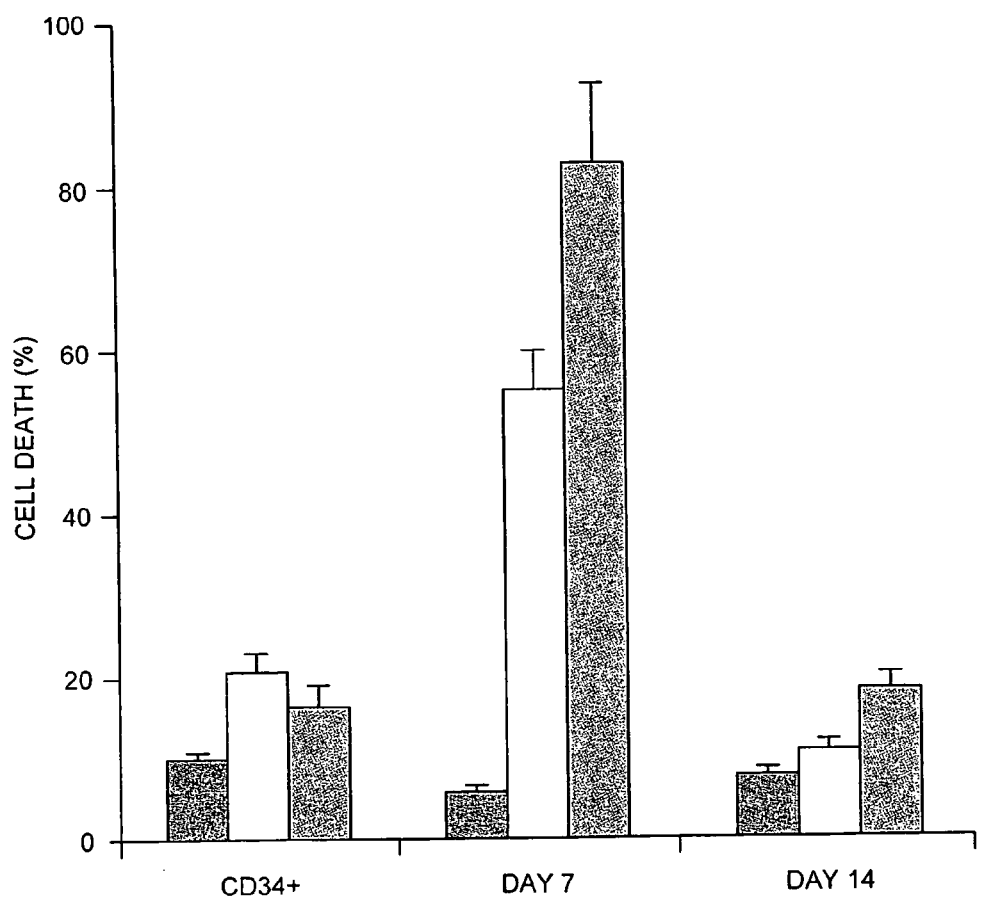

Pietsch et al. "Expression of the c-Kit receptor and its ligand SCF in non-small-cell lung carcinomas" Int. J. Cancer 75:171-175 (1998).

Singer et al. "Expression of tyrosine kinases in human malignancies as potential targets for kinase-specific inhibitors" Endocrine-Related Cancer 11:861-869 (2004).

Orazi et al. "In vivo effects of recombinant human stem cell factor treatment: A morphologic and immunohistochemical study of bone marrow biopsies" Am. J. Clin. Pathol. 103:177-184 (1995).

Schwartz et al. "Expression of the C-kit receptor (CD117) is a feature of almost all subtypes of de novo acute myeloblastic leukemia (AML), including cytogenetically good-risk AML, and lacks prognostic significance" Leuk. Lymphoma 34:85-94 (1999).

Tong et al. "In vivo administration of recombinant methionyl human stem cell factor expands the number of human marrow hematopoietic stem cells" Blood 82:784-791 (1993).

Went et al. "Prevalence of KIT expression in human tumors" J. Clin. Oncol. 22:4514-4522 (2004).

Zeuner et al. "Stem cell factor protects erythroid precursor cells from chemotherapeutic agents via up-regulation of BCL-2 family proteins" Blood 102:87-93 (2003).

Zeuner et al. "Chemotherapy-Induced thrombocytopenia derives from the selective death of megakaryocyte progenitors and can be rescued by stem cell factor" Cancer Res. 67:4767-4773 (2007).

Crawford et at "A phase I trial of recombinant methionyl human stem cell factor in patients with advanced non-small cell lung carcinoma" Proc. Am. Soc. Clin. Oncol. 12:135, abstract 338 1993.

Demetri et al. "A phase I trial of recombinant methionyl human stem cell factor (SCF) in patients with advanced breast carcinoma pre- and post-chemo-therapy with cyclophosphamide and doxorubicin" Proc. Amer. Soc. Clin. Oncol. 12:142, abstract 367(1993).

Zeuner et al. "Stem cell factor upregulates BCL-2 gamily members and protects erythroid precursor cells from chemotherapy-induced apoptosis" The Third European Workshop on Cell Death, Salobreña, Spain, Abstract, Feb. 23-28 (2002).

Amgen "Product Monograph STEMGEN®" pp. 1-22 (Apr. 2004).

* cited by examiner

STEM CELL FACTOR FOR PREVENTING CHEMOTHERAPY-INDUCED DEPLETION OF BLOOD CELLS

This application is the US national phase of International Application No. PCT/IB03/00930 filed in English on 14 Feb. 2003, which designated the US. The entire contents of this application is incorporated herein by reference.

The present invention relates to the use of Stem Cell Factor in the protection of progenitor cells and in the prevention of chemotherapy-induced depletion of blood cells.

Suppression of red blood cell production is a common complication of chemotherapy, causing anemia, thrombocytopenia, neutropenia and lymphocytopenia in a significant number of cancer patients. Thus, depletion of blood cells is a common complication of cancer, often resulting in a significant decrease of quality of life and influencing the outcomes of patients care. The myelosuppressive effects of chemotherapy are a major cause of anemia, immunodeficiency and coagulation problems in cancer patients. While inducing apoptosis in malignant cells, anticancer drugs appear to interfere with the normal production of bone marrow cells. Specifically, it is unknown if chemotherapy-induced anemia, thrombocytopenia, neutropenia and lymphocytopenia are the result of a generalized suppression of hematopoiesis occurring at the level of bone marrow progenitor/stem cell compartment or if differentiated hematopoietic precursors are directly affected by the toxic effects of antineoplastic drugs. Currently available supportive therapies are based on the use Epo (Erythropoietin) and G-CSF to help the repopulation of the erythroid and granulocytic compartment after chemotherapy. However, these compounds do not prevent the depletion of hematopoietic cells caused by antineoplastic treatment and are only moderately effective in limiting the consequences of anemia and neutropenia. Erythroid progenitor cells originate from the stem cell pool in the bone marrow and enter a differentiation/maturation process that is primed by early acting cytokines such as stem cell factor (SCF; also known as kit ligand or steel factor) and interleukin-3 (IL-3) and lately orchestrated by Epo. Expansion of the erythroid compartment is controlled by positive and negative signals operating on immature erythroblasts which are Epo-dependent and highly susceptible to apoptosis.

To identify the preferential target of chemotherapy-induced erythroid suppression, we investigated the effects of antineoplastic drugs on highly purified populations of hematopoietic progenitors and erythroid precursors. We show that immature erythroblasts are an extremely sensitive target of cytotoxic drugs and that SCF protects these cells from chemotherapy-induced apoptosis. We also demonstrate that SCF inhibits drug-induced caspase activation in erythroid precursors and upregulates Bcl-2 and Bcl-$X_L$ proteins, which protect erythroblasts from chemotherapeutic agents. The results presented identify SCF as a protective factor for erythroid cells during chemotherapy and thus a particular use of this cytokine in the supportive care of anemic cancer patients.

Accordingly, the present invention provides the use of Stem Cell Factor, in the manufacture of a medicament for the prevention of chemotherapy-induced depletion of blood cells.

Stem Cell Factor is also known as Steel Factor, mast cell growth factor and/or c-Kit ligand. It is a well known haematopoietic growth factor with a molecular weight of 18.6 KD, determined from its sequence. It is found naturally as a dimer (35 KD protein, 53 KD in its glycosylated form).

Stem Cell Factor is described in WO 92/00376 and in EP-A-423980, both of which are incorporated herein in their entirety.

Stem Cell Factor can be identified (as well as isolated) by standard procedures in the art, including a biological assay such as a growth factor-dependent mast cell line to look for cell proliferation. Any IL-3 dependent cell line expressing c-Kit can be used to provide responder cells for a proliferation assay receptor or binding assay for a mammalian MGF. WO 92/00376 describes Stem Cell Factor in full and refers to a Stem Cell Factor clone 10 deposited with the ATCC on Sep. 11, 1990 under accession number 68396). Stem Cell Factor can be defined as a family of mammalian polypeptides which are capable of stimulating IL-3 dependent mast cell lines and hematopoietic progenitor cells, and serve as a ligand for the gene product of the c-Kit proto-oncogene. As used herein, the term Stem Cell Factor includes analogs and subunits of such polypeptides with substantially similar polypeptide sequences and which bind to the protein expressed by the c-Kit proto-oncogene and which induce proliferation of mast cells, e.g. IL-3 dependent murine mast cell line MC6 or human cell line TF1.

In the present text, the term "prevention" includes preventing the development of the problem or disease as well as reducing or ameliorating the development of the disorder or the disease. Accordingly, the term "prevention" is not limited to absolute prevention.

The term chemotherapy-induced depletion of blood cells includes chemotherapy-induced anemia, chemotherapy-induced neutropenia, chemotherapy-induced lymphocytopenia and chemotherapy-induced thrombocytopenia. Neutrotopenia is the decrease in the number of neutrophils. Lymphocytopenia is the decrease in the number of lymphocytes. Thrombocytopenia is the decreased number of platelets.

The present invention may be used to prevent chemotherapy-induced depletion of blood cells. The chemotherapy may be any, including chemotherapy which comprises the use of one or more of Cisplatin, Camptothecin, Etoposide, Daunorubicin or Vincristine. In accordance with the present text, chemotherapy includes cytotoxic compounds. Preferably, the present invention relates, in all aspects, to protection of blood cells during cancer-based chemotherapy.

The present invention also relates to the use of Stem Cell Factor in the manufacture of a medicament for the prevention of death of hematopoietic progenitor cells. According to this text, progenitor cells include cells which develop into progenitor cells (in particular stem cells) and includes cells which develop from progenitor cells (known often as precursor cells) and also mature cells developed therefrom). The progenitor population includes multipotent progenitor cells (which make cells of different hematopoietic lineages), bipotent progenitors (which make cells of two lineages, such as erythroid and megakaryotic) or progenitors able to produce a single type of precursor (that is erythroid). The progenitor cells include hematopoietic progenitor cells. It appears from this invention that Stem Cell Factor protects all hematopoietic cells expressing the c-Kit (SCF receptor). In particular, the progenitor cells or the precursors thereof may be one or more of erythroid cells, granulocytic cells, monocytic cells, stem cells, lymphocytic cells or megakaryocytic cells.

The use of Stem Cell Factor according to the present invention may be in combination with another pharmaceutically active agent. The other pharmaceutically active agent may be proerythroid. Examples of such other pharmaceutically active agents include Erythropoietin, Erythropoietin derivatives, a cytokine, a kinase or indeed any other pharmaceutically active agent. Cytokines may include interleukines (IL), such as IL-1 (α or β), IL-2, IL-3, IL-4, IL-5, IL-6, IL-7, IL-8, IL-9, IL-10, IL-11 or indeed any individual interleukin from IL-1 to IL-23. Kinases include fms-like tyrosine kinase. Erythropoietin derivatives include Erythropoietin alpha (a commercial derivative of Erythropoietin). Other pharmaceutically active agents include colony stimulating factors (CSFs), including granulocyte-CSF, CSF-1, GM(macrophage)-CSF or macrophage-CSF, as well as Leukemic Inhibitory Factor (LIF). Epo is erythropoietin and is a well known polypeptide, such as described in Rizzo J D, Lichtin A E, Woolf S H, Seidenfeld J, Bennett C L, Cella D, Djulbegovic B, Goode M J, Jakubowski A A, Lee S J, Miller C B, Rarick M U, Regan D H, Browman G P, Gordon M S; American Society of Clinical Oncology; American Society of Hematology. Use of epoetin in patients with cancer: evidence-based clinical practice guidelines of the American Society of Clinical Oncology and the American Society of Hematology. Blood 100:2303-20 (2002).

The present invention shows that Stem Cell Factor, in combination with another pharmaceutically active agent, can have a synergistic effect in the prevention of chemotherapy-induced depletion of blood cells and in the prevention of death of progenitor cells.

The present invention also relates to a method for preventing chemotherapy-induced depletion of blood cells in a patient, the method comprising administering Stem Cell Factor to said patient.

Said patient is preferably a patient in need thereof. The patient is preferably a human.

The present invention also relates to a method for the prevention of death of progenitor cells in a patient, the method comprising administering Stem Cell Factor to said patient.

Again, preferably said patient is in need thereof. Preferably said patient is a human.

As previously described in relation to the invention, the Stem Cell Factor may be administered in combination with another pharmaceutically active agent. The other pharmaceutically active agent may be administered simultaneously, sequentially or separately to the Stem Cell Factor.

Depletion of the stem/progenitor cell compartment is frequently observed after multiple cycles of chemotherapy for cancer treatment. Although resting hematopoietic stem and progenitor cells are scarcely susceptible to chemotherapy, we observe that hematopoietic stem and progenitor cells, identified with the marker CD34, have an increased sensitivity to chemotherapic agents in proliferative conditions. We find that SCF protects in vitro CD34 positive cells from the cytotoxic activity of chemotherapeutic agents, such as Cisplatin, Etoposide and Daunorubicin. The protective effect of SCF is even more evident if CD34 positive cells are induced to proliferate by exposure to cytokines, such as interleukin-3 (50 units/mL) and fms-like tyrosine kinase 3 (100 nanograms/mL) (i.e. about 50% of CD34 positive cells treated with SCF survive to 3 micrograms/mL Cisplatin, while virtually all cells die in its absence). Moreover, after removal of chemotherapeutic drugs, those cells that have been treated with SCF are able to expand and give rise to all the standard hematopoietic populations in clonogenetic assays. Thus, SCF can protect multiple normal hematopoietic cell types during chemotherapy and decrease significantly the blood cell depletion associated to chemotherapy. The ability of SCF to protect hematopoietic stem/progenitor cells from chemotherapy indicates that all their progeny can benefit from SCF treatment.

The present invention also relates to a method for preventing chemotherapy-induced depletion of blood cells in vitro, the method comprising administering Stem Cell Factor to cells in an in vitro environment. Such a method may be useful where cells or tissues are extracted from a patient, undergo one or more rounds of chemotherapy and are then placed or inserted back into said patient.

The present invention also relates to a kit, comprising Stem Cell Factor and another pharmaceutically active agent, for use in preventing chemotherapy-induced depletion of blood cells. The Stem Cell Factor and other pharmaceutically active agent components of the kit may be administered simultaneously, sequentially or separately.

It should be noted that in accordance with the present invention, the Stem Cell Factor is used to prevent death of progenitor cells. This enables its use in the prevention of chemotherapy-induced depletion of blood cells. This differentiates the use from proliferation of cells, where the progenitor cells thereof may still undergo cell death and the patient will not be protected from chemotherapy-induced anemia or thrombocytopenia.

The concentrations of Stem Cell Factor and other pharmaceutically active agent in accordance with this text are based on their inherent properties with effectively no reduction of their activity by denaturisation or destabilisation. Thus, the concentrations of Stem Cell Factor and other pharmaceutically active agent which are provided are not absolute, but reflect their inherent activity. Various modifications or recombinant Stem Cell Factor and other pharmaceutically active agent can be utilised as long as they have the same protective activity against multipotent progenitor cells or the precursors thereof.

For each aspect of the invention which may be involved in medicine or involve any administration to biological tissue (including patients), the particular dated regime will ultimately be determined by the attending physician and will take into consideration such factors as the chemotherapeutic regime being administered and the likelihood or previous history of the patient suffering in relation to chemotherapy-induced anemia. The particular dosage regime according to the present invention will ultimately be determined by the attending physician and will take into consideration factors such as those described above and also animal type, age, weight, severity of symptoms and/or severity of treatment being or to be applied, method of administration, adverse reactions and/or other contraindications. Specific defined dosage ranges can be determined by standard designed clinical trials with patient progress and recovery being fully monitored. Such trials may use an escalating dose design using a low percentage of the maximum tolerated dose in animals as the starting dose in man. Preliminary guidance for dosage ranges can be taken from the results given in the experimental section of this text and by the following. As an example of possible suitable ranges it is known that recombinant human SCF has been used in clinical trials (for increasing proliferation and mobilization of Stem and progenitor cells) in doses ranging between 5 and 50 micrograms/kg/day. In these trials, patients were premedicated with antiallergy prophylaxis.

The medicaments for all aspects of the present invention can be used to provide the required concentration of Stem Cell Factor (optionally with another pharmaceutically active agent) in one or more "intake" per day ("intake" including any form of administration and also describing a dosage unit). Some aspects of the invention may suit a single intake of a high Stem Cell Factor concentration, whereas others may suit a number of intakes, evenly or unevenly spaced over the same period, but with a lower Stem Cell Factor concentration per intake.

Use of the Stem Cell Factor, optionally in combination with another pharmaceutically active agent (including the manufacture of medicaments) according to the present invention may be in combination with a suitable pharmaceutical carrier and/or excipient. Such carriers and excipients are well known in the art (e.g. Handbook of Pharmaceutical Excipients (1994), second edition, Eds. A Wade/P J Weller, The Pharmaceutical Press, American Pharmaceutical Association). Of particular, use according to the present invention are compositions and/or medicaments which are formulated for subcutaneous delivery, as for Epo and G-CSF. However, alternative routes may be utilised.

Preferably, the Stem Cell Factor for use according to the present invention is administered before and/or during chemotherapy. The administration of Stem Cell Factor may continue after the removal of the chemotherapeutic drugs. Most preferably, the Stem Cell Factor is administered both before and during administration of the chemotherapy.

The start and duration of the administration of Stem Cell Factor depends on various factors, as described above. When administered before chemotherapy, preferably the Stem Cell Factor is administered for at least 0.5, 1, 1.5 or 2 hours. The length of administration before chemotherapy may vary and may include the delivery up to around 48 hours before chemotherapy. If the Stem Cell Factor is administered during chemotherapy, it is preferably administered for the duration of the chemotherapy. Particularly useful may be the maintenance of Stem Cell Factor after chemotherapy. The duration of this may vary. The duration may include maintaining Stem Cell Factor for up to 24 hours or from 24-72 hours after chemotherapy for a further increase in cell survival.

The medicinal use of SCF is known. The administration of SCF is generally well tolerated, adverse reactions can be prevented by antiallergic medicaments.

Purified populations of hematopoietic progenitors and precursors are routinarily obtained in our laboratory through purification of CF34+ cells from peripheral blood and culture in serum-free medium with unilineage growth factors. Hematopoietic progenitor cells display different sensitivity to the cytotoxic effect of chemotherapeutic agents depending on their lineage commitment and stage of maturation. We have observed that SCF treatment of erythroid and granulocytic precursor cells, as well as of uncommitted CD34+ progenitors, results in a strong protection from death induced by different categories of antineoplastic agents. The protective effects of SCF are achieved by administrating this cytokine before the cytotoxic treatment, during the course of the treatment itself and after the toxic stimulus has been interrupted. Following removal of the chemotherapeutic agent, SCF-treated cells regain full proliferative activity, being able to expand at levels comparable to cells that were not exposed to the cytotoxic treatment. Importantly, once the toxic stimulus has been removed, SCF-treated cells re-enter the differentiative pathway, maintaining their ability to complete successfully the normal maturation process. Conversely, cells that did not receive SCF die extensively in response to antineoplastic drugs and they are not able to expand at significant levels after removal of the apoptotic stimulus.

In order to elucidate the mechanisms responsible for the protective effect of SCF from chemotherapy-induced cell death, we analysed the expression of pro- and anti-apoptotic genes in SCF-treated erythroid precursor cells. SCF induced an upregulation of anti-apoptotic genes belonging to the Bcl-2 family and to the Notch family, as well as an increase in the levels of several transcription factors involved in the control of cellular proliferation and survival. Gene transfer experiments in CD34+ hematopoietic progenitors have confirmed that genes upregulated by SCF confer resistance to chemotherapy-induced apoptosis.

In accordance with the present text, all preferred features of the different aspects of the invention apply to each other mutatis mutandis.

The present invention will now be described with reference to the figures, in which the following are the legends:

FIG. 1. Chemosensitivity of $CD34^+$ progenitors and erythroid precursors. Highly purified populations of erythroid precursors were obtained by unilineage culture of peripheral blood $CD34^+$ cells and analyzed at day 7 and day 14 of differentiation. Cells were incubated with erythroid medium alone (black bars), with 1.5 μg/ml cisplatin (white bars) or 50 ng/ml camptothecin (grey bars) for 24 hours. The percentage of cell death was evaluated by ethidium bromide/acridine orange staining. The results shown are the mean±s.d. of four independent experiments performed with cells from different donors.

Figure 2:
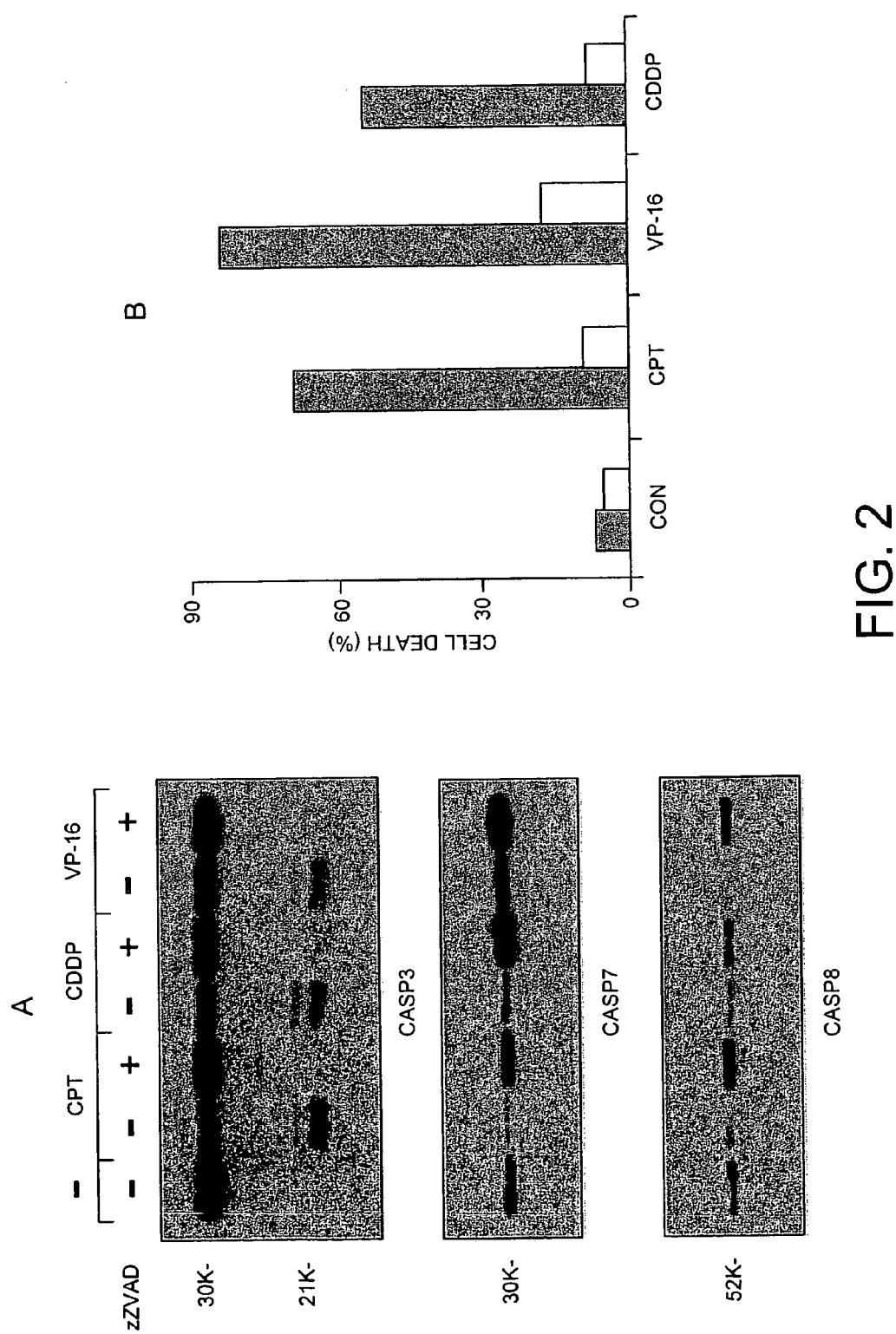

FIG. 2. Drug-induced apoptosis of erythroid precursor cells is mediated by caspase activation. (A) Chemotherapeutic agents activate caspases in immature erythroblasts. Erythroblasts at day 7 of differentiation were stimulated with 200 ng/ml camptothecin (CPT), 3 μg/ml cisplatin (CDDP) or 5 μM etoposide (VP-16) in the presence or absence of zVAD 40 μM, lysed after 8 hours and analyzed by immunoblot with antibodies against caspase 3, caspase 7 and caspase 8. (B) zVAD inhibits apoptosis induced by chemotherapeutic agents. Day 7 erythroblasts were stimulated with 50 ng/ml camptothecin (CPT), 3 μg/ml cisplatin (CDDP) or 2 μM etoposide (VP-16) in the presence (white bars) or in the absence (black bars) of zVAD 40 μM. After 24 hours the percentage of cell death was determined by ethidium bromide/acridine orange staining. A typical experiment of five performed with cells from different donors is shown.

Figure 3:
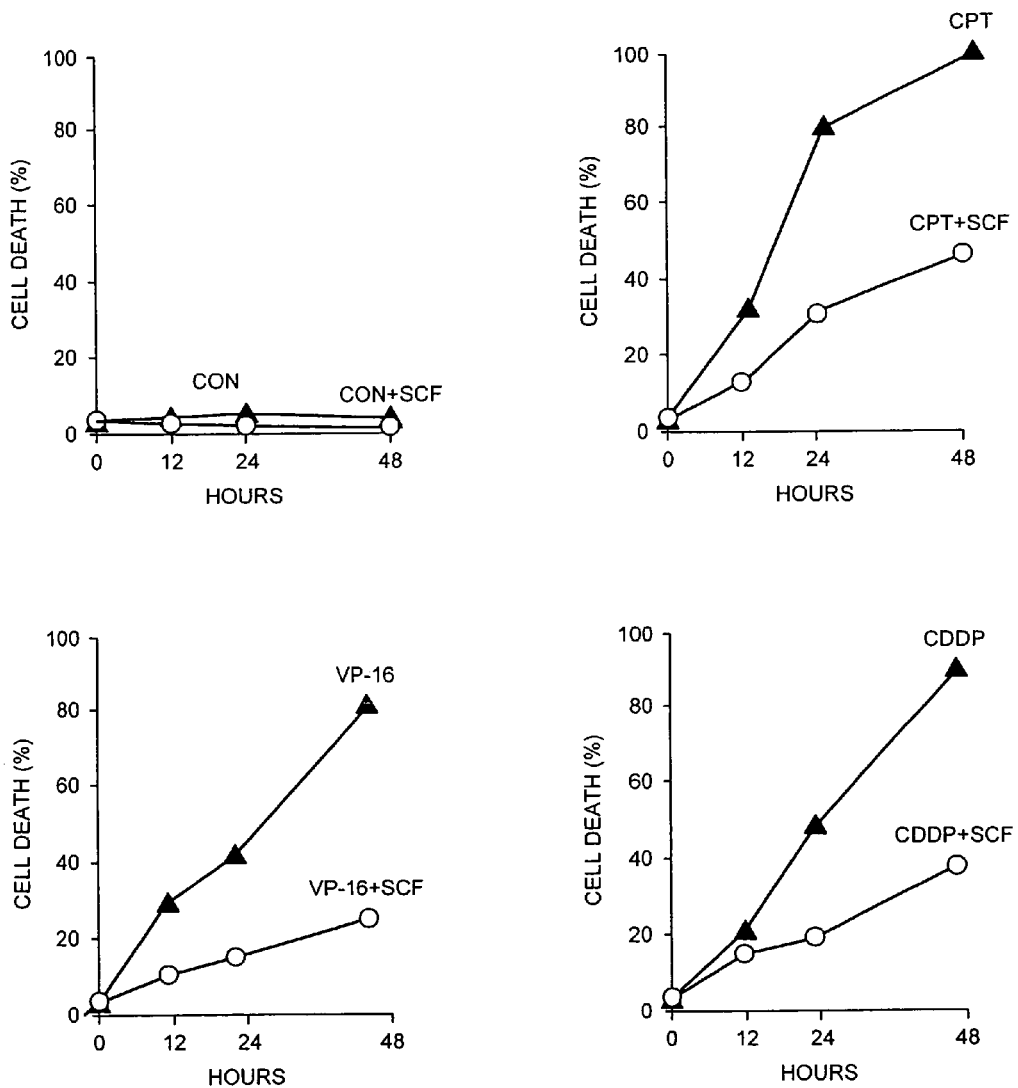

FIG. 3. SCF protects erythroid precursors from drug-induced apoptosis. Day 7 erythroblasts were incubated with 50 ng/ml camptothecin (CPT), 2 μM etoposide (VP-16) or 3 μg/ml cisplatin (CDDP) in standard erythroid medium and the percentage of cell death was determined after 12, 24 and 48 hours. Where indicated (+SCF) cells were preincubated for two days with 100 ng/ml SCF and kept in the presence of SCF during incubation with chemotherapeutic drugs. A typical experiment of six performed with cells from different donors is shown.

Figure 4:
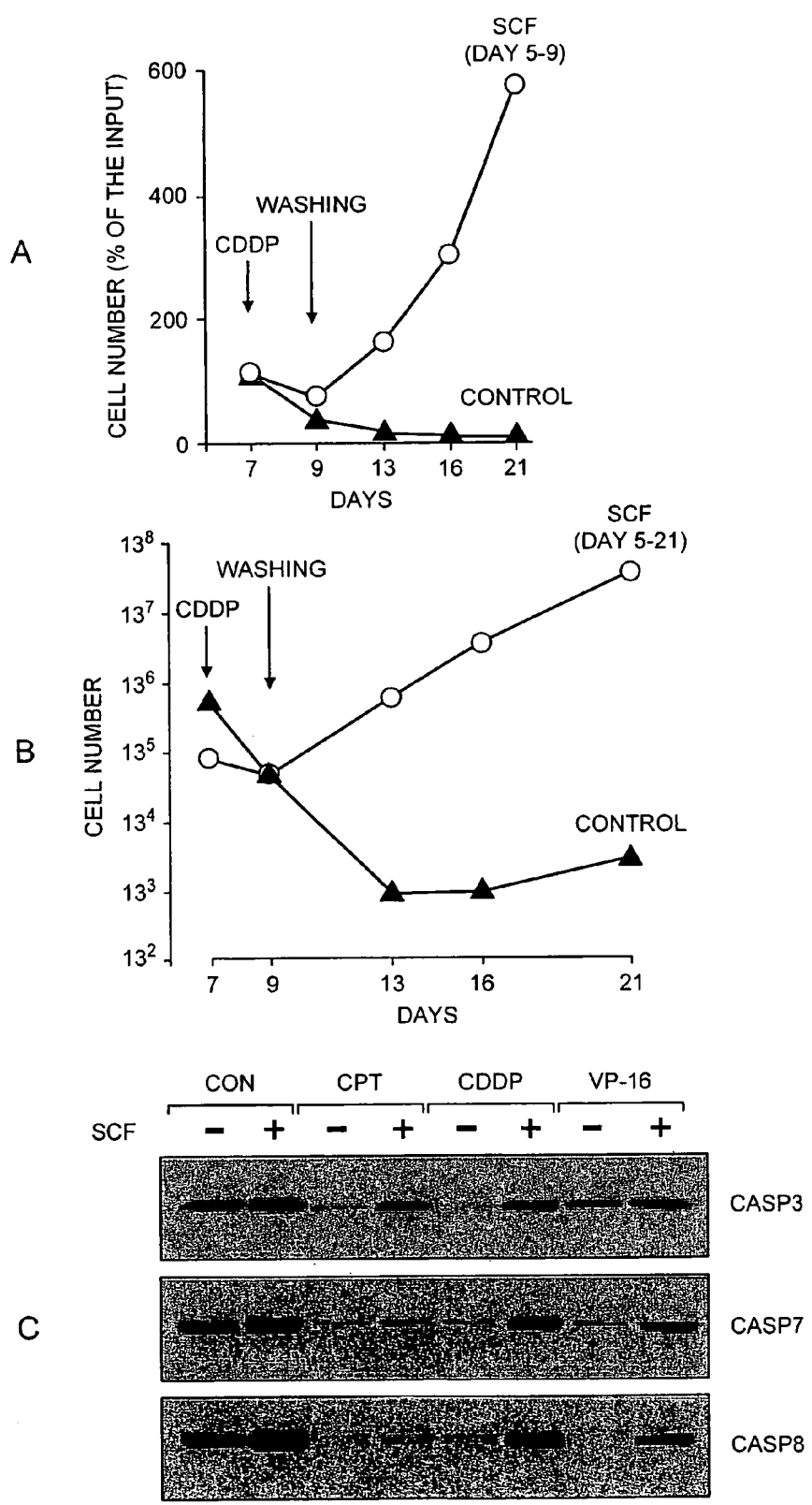

FIG. 4. Erythroblasts treated with SCF are able to expand after removal of chemotherapeutic drugs and have lower levels of drug-induced caspase activation. (A) Day 7 erythroblasts, untreated (Control) or pretreated for two days with 100 ng/ml SCF (SCF day 5-9), were exposed to 3 μg/ml cisplatin (CDDP) for 48 hours, washed and placed in fresh medium with or without SCF, which was maintained in the culture medium until day 9. (B) Day 7 erythroblasts, untreated (Control) or pretreated for two days with SCF (SCF day 5-21) were exposed to cisplatin as above. After 48 hours, $4\times10^4$ cells were washed and replated in standard erythroid medium with or without 100 ng/ml SCF. In order to obtain equal numbers of erythroblasts after the cytotoxic treatment, a higher number of control cells was plated at the beginning of the experiment. (C) Western blot analysis of caspases in immature erythroblasts untreated (Con) or pretreated for two days with SCF and exposed for 8 hours to camptothecin (CPT), cisplatin (CDDP) and etoposide (VP-16), showing the proforms of caspase 3 (top panel), caspase 7 (middle) and caspase 8 (bottom). One representative experiment out of four performed with cells from different donors is shown.

Figure 5:
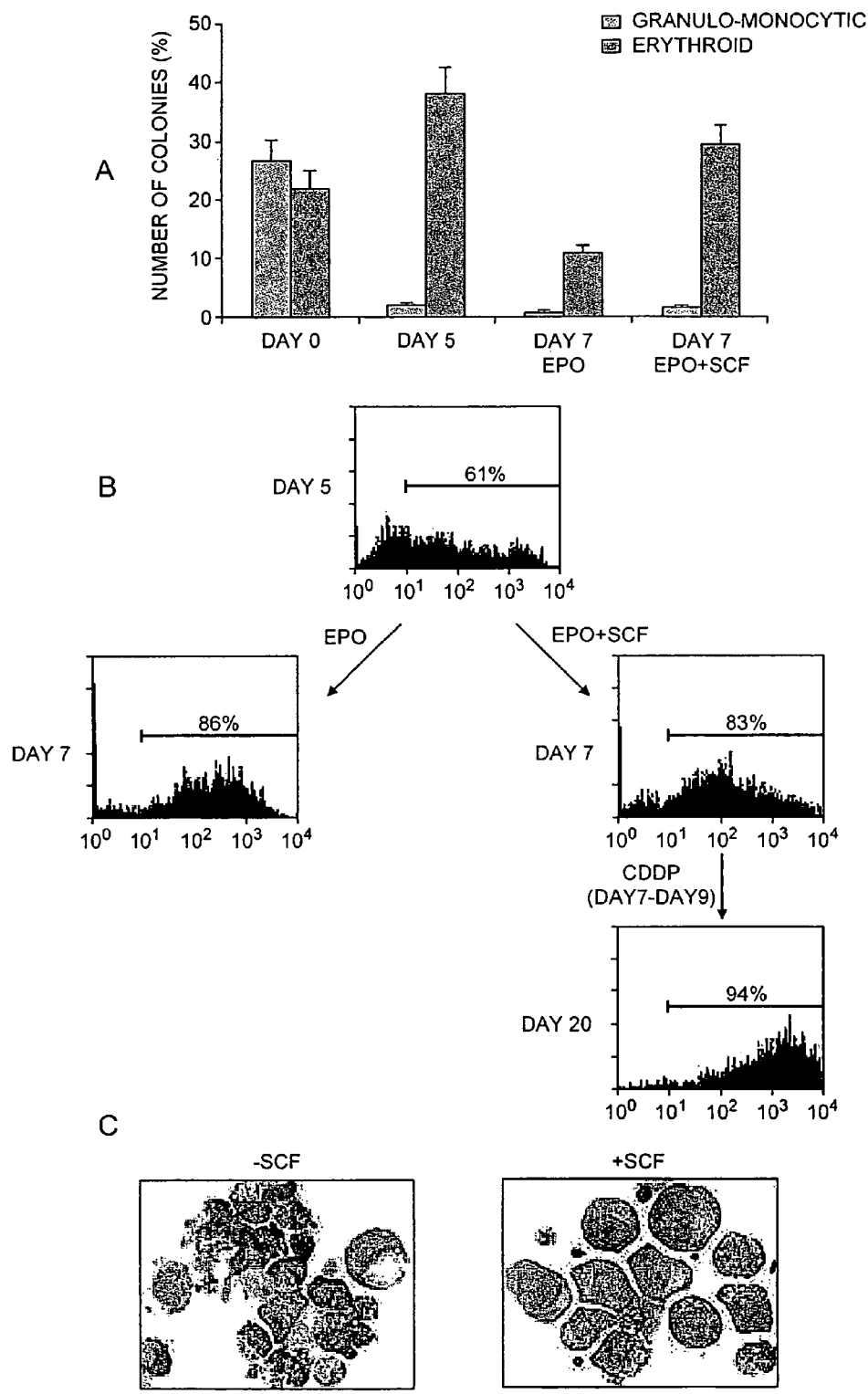

FIG. 5. SCF does not promote the growth of non-erythroid cells in erythroid unilineage culture. (A) Clonogenetic assay of $CD34^+$ cells (day 0) or cells grown in liquid culture and subsequently plated in semisolid medium at day 5 or day 7 of erythroid differentiation. Control cells (day 5 and day 7 Epo) were cultivated in standard erythroid medium before the colony assay, whereas SCF-treated cells (day 7 Epo+SCF) received 100 ng/ml SCF from day 5 to day 7 of liquid culture. (B) Cytofluorimetric analysis of glycophorin A-positive cells in erythroid unilineage culture. Cells were analyzed after five (day 5) or seven days (day 7) of erythroid differentiation in standard erythroid medium (Epo) or in the same medium supplied with 100 ng/ml SCF starting from day 5 (Epo+SCF). At day 7, cells were treated with cisplatin (CDDP day 7-day 9), and SCF-treated cells that survived the treatment were analyzed at day 20 of culture in standard erythroid medium supplemented with SCF. (C) May-Grünwald-Giemsa staining of day 7 erythroid cells treated with cisplatin for 48 hours in standard erythroid medium alone (−SCF) or with 100 ng/ml SCF (+SCF), which was supplied two days before and during the cytotoxic treatment.

Figure 6:
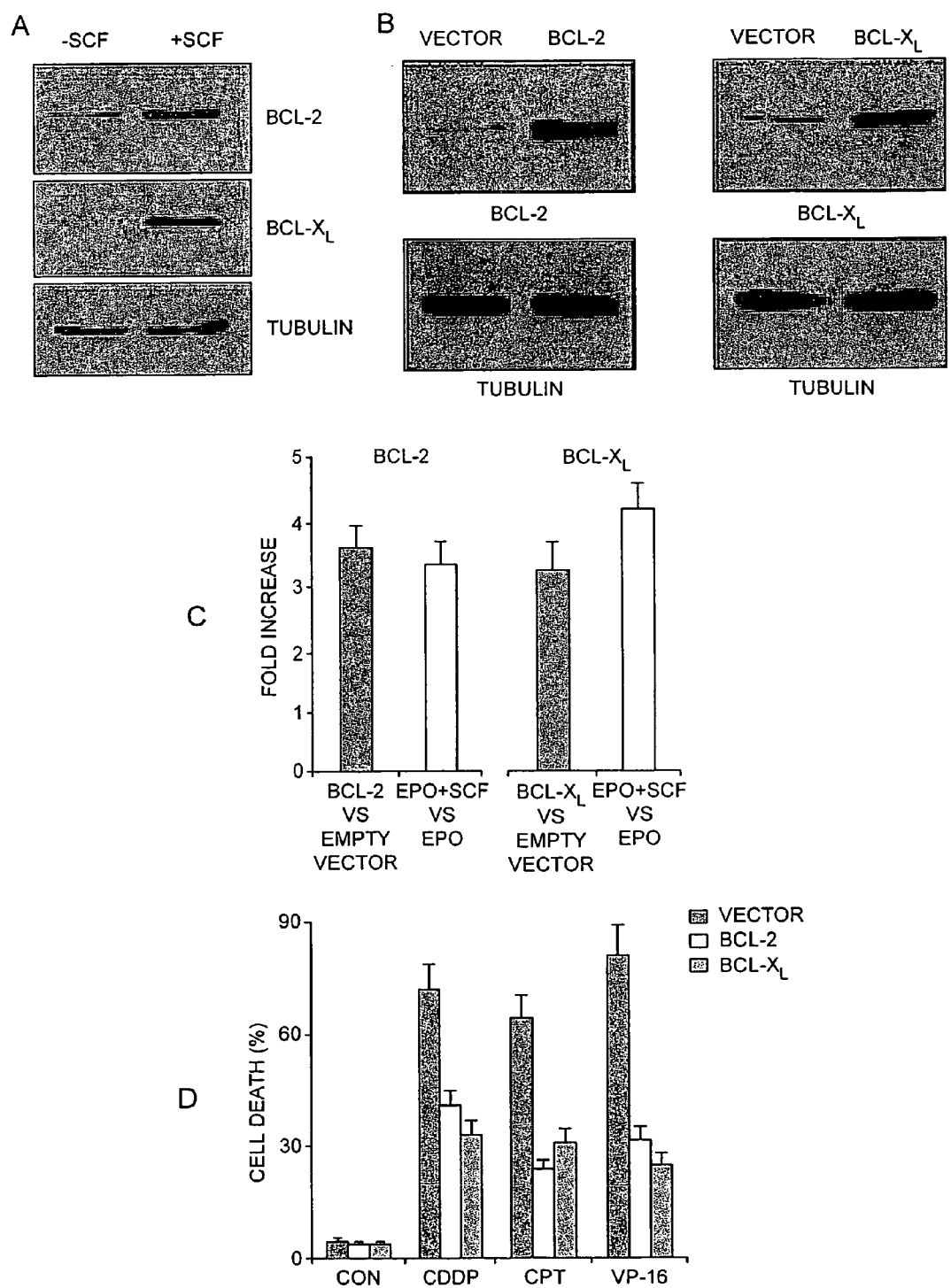

FIG. 6. SCF upregulates Bcl-2 and Bcl-$X_L$, which are able to protect erythroblasts from apoptosis induced by chemotherapeutic drugs. (A) Western blot analysis of Bcl-2 and Bcl-$X_L$ levels in day 7 erythroblasts cultured in standard erythroid medium (−SCF) or preincubated from day 5 to day 7 in erythroid medium supplemented 100 ng/ml SCF (+SCF). (B) Western blot analysis of erythroblasts transduced with empty vector, Bcl-2 or Bcl-$X_L$. Cycling CD34$^+$ cells were transduced with a retroviral vector containing cDNAs for Bcl-2 or Bcl-$X_L$ and GFP as a reporter gene. Cells were sorted for GFP expression, placed in standard erythroid medium and analyzed at day 4 of differentiation. One representative experiment out of five performed with cells from different donors is shown. (C) Comparison of Bcl-2 or Bcl-$X_L$ expression in SCF-treated erythroblasts (Epo+SCF) versus erythroblasts grown in standard medium and transduced with Bcl-2 or Bcl-$X_L$. Data show the increase in gene-transduced erythroblasts as compared to empty vector-transduced erythroblasts (filled bars) or in SCF-treated versus untreated erythroblasts (open bars). (D) Cells transduced with empty vector (black bars), Bcl-2 (white bars) or Bcl-$X_L$ (grey bars) were incubated with medium alone (Con), 50 ng/ml camptothecin (CPT), 2 µM etoposide (VP-16) or 3 µg/ml cisplatin (CDDP). The percentage of cell death was evaluated after 24 hours by staining with ethidium bromide/acridine orange. The results shown are the mean±s.d. of three independent experiments performed with cells from different donors.

The present invention will now be described with reference to the following non-limiting examples.

EXAMPLES

Example 1

Materials and Methods

Cytokines, antibodies and chemicals. Human recombinant SCF, IL-3, granulocyte-macrophage colony-stimulating factor (GM-CSF) and Flt3 ligand were purchased from Peprotech Inc. (Rocky Hill, N.J.). Recombinant human Epo was supplied by Amgen (Thousand Oaks, Calif.). Polyclonal antibody against caspase 3 (65906E) was from BD Pharmingen (San Diego, Calif.), anti-caspase 8 (clone 5F7) was from Upstate Biotechnology (Lake Placid, N.Y.) and anti-caspase 7/Mch3 was from BD Transduction Laboratories (San Diego, Calif.). Anti Bcl-2 antibody was from BD Pharmingen and anti Bcl-$X_L$ (H5) was from Santa Cruz (Santa Cruz, Calif.). zVAD-fmk was purchased from Bachem (Bubendorf, Switzerland). Anti-tubulin antibody and chemotherapeutic drugs were purchased from Sigma-Aldrich Inc. (Saint Louis, Mo.). Anti-glycophorin A FITC (559943) was from BD Pharmingen.

Adult peripheral blood human progenitor cell (HPC) purification and culture. Adult peripheral blood was obtained from male donors after their informed consent and the approval by the Committee for Human Studies. Human CD34$^+$ precursor cells were purified from peripheral blood by positive selection using the midi-MACS immunomagnetic separation system (Miltenyi Biotec, Bergisch Gladbach, Germany) according to the manufacturer's instructions. CD34$^+$ precursors were cultured in serum-free medium supplemented with 0.01 U/ml interleukin-3 (IL-3), 0.001 ng/ml GM-CSF and 3 U/ml Epo to induce unilineage erythroid differentiation. In these culture conditions a progeny of cells 98±2% glycophorin A$^+$ is generated.[14] Alternatively, CD34$^+$ cells were kept for two days in serum-free medium supplemented with cycling growth factors (100 U/ml IL-3, 100 ng/ml Flt3 ligand, 100 ng/ml SCF) for subsequent retroviral infection. Cell viability was evaluated by ethidium bromide-acridine orange staining and fluorescence microscopy analysis.[15] The differentiation stage of erythroid precursor cells was evaluated by May-Grünwald-Giemsa staining and cytologic analysis. Ziegler B, Testa U, Condorelli G, Vitelli L, Valtieri M, Peschle C. Unilineage hematopoietic differentiation in bulk and single cell culture. Stem Cells. 1998; 16(suppl 1):51-73. For clonogenetic assay, $10^2$ CD34$^+$ cells and $2\times10^2$ cells from day 5 or day 7 unilineage erythroid cultures were plated in duplicate in 0.9% methylcellulose containing 40% FCS and saturating concentrations of erythropoietin (3 U/mL), TPO (50 ng/mL), granulocyte macrophage-colony stimulating factor (GM-CSF; 10 ng/mL), M-CSF (250 U/mL), G-CSF (500 U/mL), IL-6 (10 ng/mL), stem cell factor (100 ng/mL), Flt3 ligand (100 ng/mL), and IL-3 (100 U/mL). Colonies were scored after 14 days of culture at 37° C. in a 5% $CO_2$/5% $O_2$/90% $N_2$ humidified atmosphere.

Western blotting. For detection of caspases, protein extracts were prepared by resuspending cell pellets in 1% NP40 lysis buffer (20 mM Tris/HCl pH 7.2, 200 mM NaCl, 1% NP40) in the presence of 1 mM phenylmethylsulphonyl fluoride (PMSF) and 2 µg/ml each of leupeptin, aprotinin and pepstatin. Concentration of lysates was determined by the Bradford assay (Bio-Rad Laboratories, Richmond, Calif.) and equal amounts of proteins were used for SDS-PAGE. Samples were analyzed by standard immunoblot procedure and visualized by chemiluminescence (Super Signal West Pico Pierce, Rockford, Ill.). Quantification of protein expression levels was performed with the NIH IMAGE software version 1.62 (by Wayne Rasband, National Institutes of Health, Research Services Branch, NIMH).

Production of retroviral particles and transduction of hematopoietic progenitor cells. Bcl-2 and Bcl-$X_L$ cDNAs were cloned into the PINCO retroviral vector carrying the Green Fluorescent Protein (GFP) as a reporter gene. The amphotropic packaging cell line Phoenix was transfected by standard calcium-phosphate/chloroquine method, and culture supernatants containing retroviral particles were collected after 48 hours. ETC infection was performed by suspending the cells at $5\times10^4$/ml in the viral supernatant supplemented with cycling growth factors. For one cycle of infection, cells were centrifuged at 1800 rpm for 45 minutes at 32° C. and placed back in the incubator for 1 hour. Cells were subjected to three infection cycles each day for two consecutive days and then placed in growth medium supplemented with cycling growth factors for 48 hours before sorting. GFP-positive cells were separated by flow cytometry using a FACS-Vantage (Becton Dickinson, Omaha, Calif.).

Immediately after sorting, hematopoietic progenitor cells were placed in serum-free medium supplemented with erythroid growth factors to obtain virtually pure erythroblast populations.

Results and Discussion

Immature erythroblasts are the preferential target of chemotherapeutic drugs in unilineage erythropoietic culture. To identify the cellular target of erythroid suppression induced by antineoplastic agents, we analyzed the chemosensitivity of hematopoietic CD34+ progenitors, as compared with highly purified populations of erythroblasts at different maturation stages generated from CD34+ cells in erythroid specific medium (De Maria R, Testa U, Luchetti L, Zeuner A, Stassi G, Pelosi E, Riccioni R, Felli N, Samoggia P, Peschle C. Apoptotic role of Fas/Fas ligand system in the regulation of erythropoiesis. Blood. 1999; 93:796-803, De Maria R, Zeuner A, Eramo A, Domenichelli C, Bonci D, Grignani F, Srinivasula S M, Alnemri E S, Testa U, Peschle C. Negative regulation of erythropoiesis by caspase-mediated cleavage of GATA-1. Nature. 1999; 401:489-493, Ziegler B, Testa U, Condorelli G, Vitelli L, Valtieri M, Peschle C. Unilineage hematopoietic differentiation in bulk and single cell culture. Stem Cells. 1998; 16(suppl 1):51-73). Cytotoxic drugs were used at doses compatible with their in vivo levels during cancer treatment. CD34+ progenitors, day 7 (>70% pro/basophilic) and day 14 (>80% orthochromatic) erythroblasts were incubated for 24 hours with cisplatin or camptothecin in standard erythroid medium. Evaluation of cell death revealed that CD34+ cells exhibited a modest sensitivity to drug-induced apoptosis (FIG. 1). Despite the presence of saturating concentrations of Epo, immature erythroblasts were extremely sensitive to the cytotoxic effect of chemotherapeutic agents, while becoming almost completely resistant at the advanced (orthochromatic) stage of maturation (FIG. 1). Thus, pro/basophilic erythroblasts likely represent the primary target of chemotherapy-induced anemia.

Chemotherapy-induced erythroblast apoptosis is mediated by caspase activation. Apoptosis induced by cytotoxic drugs has been shown to depend critically on activation of caspases in many cellular systems. Therefore, we analyzed caspase activation by immunoblot in immature erythroid precursors treated with cisplatin, camptothecin or etoposide. All the three drugs activated caspase 3, 7 and 8, as deduced by detection of procaspases and their active fragments (FIG. 2A). The pan-caspase inhibitor zVAD abolished caspase activation and abrogated completely chemotherapy-induced erythroblast death (FIG. 2B), indicating that caspases are key effectors of drug-induced apoptosis in erythroid precursors.

To determine whether SCF is capable of protecting erythroblasts from the effects of cytotoxic drugs, we pretreated immature erythroblasts at day 5 of differentiation with SCF for 48 hours before exposure to chemotherapeutic agents. The concentration of SCF used in all the experiments was 100 ng/ml, as this dose has been shown to support maximal erythroid proliferation in vitro. Cells pretreated with SCF and exposed to camptothecin, cisplatin or etoposide were significantly protected from the toxic effects of antineoplastic drugs (FIG. 3), suggesting that SCF interferes with the apoptotic program activated by chemotherapeutic agents in erythroid precursor cells.

SCF promotes erythroblast recovery and expansion after removal of chemotherapeutic drugs. To analyze the long term effects of SCF-mediated inhibition of erythroblast apoptosis, immature erythroid precursors untreated or pretreated for two days with SCF were exposed to cisplatin, washed after 48 hours and placed in fresh medium. Whereas in standard erythroid medium control cells were not able to recover from the toxic effects of chemotherapy, erytbroblasts preincubated with SCF showed an enhanced survival to cisplatin treatment and regained full proliferative activity after removal of the cytotoxic agent (FIG. 4A). SCF enhances proliferation and delays differentiation of erythroid cells in culture. During the two-day exposure to chemotherapeutic drugs, SCF-treated erythroblasts are significantly protected from apoptosis, but do not proliferate. However, the maintenance of SCF in the culture medium after removal of the chemotherapeutic agent results in a high proliferation rate of survived erythroid cells, which behaved similarly to drug-untreated cells in terms of expansion and maturation (FIG. 4B and data not shown). In contrast, erythroblasts kept in standard erythroid medium underwent massive apoptosis during cisplatin treatment, and continued to die for a few days after removal of the cytotoxic stimulus (FIG. 4B), indicating that a small portion of erythroid cells undergo a slower apoptotic process. These results suggest that SCF activates an apoptosis inhibitory mechanism that allows efficient recovery of erythroid progenitors from the toxic effects of chemotherapy.

Western blot analysis of erythroid precursors exposed to chemotherapeutic agents revealed that the amount of inactive pro-caspase 3, 7 and 8 was significantly higher in cells pretreated with SCF compared to control erythroblasts exposed to the same cytotoxic stimuli (FIG. 4C). These results suggest that signals generated by the activated c-kit receptor are able to inhibit drug-induced caspase activation in erythroid precursor cells, allowing the accomplishment of the erythropoietic process.

SCF supports the selective expansion of erythroid cells in unilineage culture conditions after treatment with chemotherapeutic agents. Theoretically, SCF may promote the growth of non-erythroid cells present in small numbers in erythroblastic cultures, and even specifically protect these contaminants from cytotoxic drugs, thus generating a post-chemotherapy population of non-erythroid cells. To rule out this possibility, we compared the number of erythroid colonies generated by SCF-treated or control cells at day 7 of erythroid culture in a semisolid medium supplied with multilineage growth factors. Two-days treatment with SCF did not significantly increase the percentage of granulo-monocytic colonies present in the culture (FIG. 5A), while exerting a significant stimulatory effect on the growth of erythroid colonies. Accordingly, cytofluorimetric analysis of glycophorin A expression on cells at day 7 of erythroid liquid culture revealed a similar percentage of glycophorin-positive cells irrespectively of two-days SCF pretreatment (FIG. 5B). Moreover, SCF-pretreated erythroblasts that survived cisplatin treatment showed glycophorin positivity and clear erythroid phenotype (FIGS. 5B and C), indicating that SCF does not promote growth and survival of non-erythroid cells in the experimental conditions used.

SCF-mediated upregulation of Bcl-2 and Bcl-$X_L$ protects immature erythroblasts from drug-induced apoptosis. The observation that drug-induced caspase activation is inhibited in cells pretreated with SCF prompted us to investigate whether this cytokine modulates the levels of proteins that influence caspase activity. Extensive western blot analysis of apoptosis-related proteins was performed on erythroblasts treated for two days with SCF as compared with cells at the same differentiation stage kept in standard erythroid medium. Among the proteins examined, we found that Bcl-2 and Bcl-$X_L$ are upregulated in SCF-treated cells, while levels of other Bcl-2 family members remain unchanged (FIG. 6A and data not shown). Since antiapoptotic Bcl-2 family proteins can indirectly prevent the activation of executioner caspases by controlling cytochrome c efflux from mitochondria, it is likely that the increased levels of Bcl-2 and Bcl-$X_L$ may explain the lower caspase activity observed in erythroblasts treated with cytotoxic drugs.

Antiapoptotic Bcl-2 family members have been implicated in modulation of apoptosis induced by chemotherapeutic drugs in several cellular systems. Therefore, we speculated that the upregulation of Bcl-2 and Bcl-$X_L$ induced by SCF in erythroid precursor cells may contribute to the cytoprotective effect of this cytokine. To determine if increased levels of Bcl-2 and Bcl-$X_L$ are sufficient to protect erythroblasts from the effects of chemotherapeutic drugs, CD34$^+$ hematopoietic progenitors were transduced with a retroviral vector containing the cDNA for Bcl-2 or Bcl-$X_L$ with the GFP as a reporter gene and subsequently sorted on the basis of GFP expression. After sorting, CD34$^+$ cells were cultured in unilineage erythroid medium until they reached the basophilic stage of differentiation and then exposed to chemotherapeutic agents. Quantitative immunoblot analysis showed that the levels of Bcl-2 and Bcl-$X_L$ obtained after retroviral transduction were comparable with those observed in SCF-stimulated erythroblasts (FIGS. 6A-C) and sufficient to significantly reduce chemotherapy-induced cell death (FIG. 6D). Thus, SCF-induced Bcl-2 and Bcl-$X_L$ upregulation likely contributes to protect immature erythroid cells from the cytotoxic effects of chemotherapeutic agents.

Myelosuppression is a major side effect of chemotherapy, often resulting in dose modification and treatment delay. Different approaches have been employed with the intent of recovering blood cell production, including the use of recombinant cytokines and transplantation of normal or genetically modified hematopoietic progenitor/stem cells.

Chemotherapy-induced anemia is very common in patients with solid tumors, and reaches the highest incidence in patients with lung cancer and gynecologic or genitourinary tumors, who require blood transfusions in 50-60% of cases. Suppression of red blood cell production caused by chemotherapeutic agents appears to involve both inhibition of erythropoiesis and reduction of serum Epo levels. Recombinant human Epo is used in several clinical settings such as the treatment of anemia associated with chronic renal failure or zidovudine therapy in HIV patients. In patients undergoing anticancer therapy, Epo administration has been shown to alleviate anemia and reduce transfusion requirements and is currently used to treat one third of patients with substantial anemia (Hb<10 g/dL) induced by chemotherapy. However, Epo treatment does not result in improvement of anemia in a consistent fraction of patients, and no reliable predictors of its therapeutic response have been found to date.

The data presented in this work suggest that SCF is useful for the treatment of chemotherapy-induced anemia in cancer patients. The use of SCF to prevent and treat chemotherapy-induced anemia can be particularly indicated in (i) adult patients not responsive to epoetin treatment, i.e. when causes of anemia are not related to inadequate Epo response, (ii) children with cancer, where anemia is associated with a decreased bone marrow erythropoietic activity and seems unrelated to defective Epo production, and (iii) patients who already receive epoetin alfa, because the synergy between Epo and SCF could achieve optimal precursor cell proliferation with reduced doses of growth factors.

The myelotoxic effects of chemotherapeutic agents involve activation of apoptotic pathways in hematopoietic cells. Our study identifies apoptosis of immature erythroblasts as a likely cause of drug-induced erythroid suppression. Therefore, strategies aimed at the prevention and treatment of chemotherapy-induced anemia should focus on this cell population, whose integrity is crucial for homeostasis of the erythroid compartment. Our work demonstrates that SCF protects immature erythroid precursors from drug-induced apoptosis. It is noteworthy that in the presence of chemotherapeutic drugs, Epo alone does not effectively protect early erythroid cells from apoptosis, whereas combined treatment with Epo and SCF induces a striking rescue of erythroblast survival and optimal expansion after drug removal. Furthermore, our studies indicate that this effect may be mediated by the upregulation of Bcl-2 and Bcl-$X_L$. This observation is in line with previous studies showing that susceptibility to drug-induced apoptosis correlates with levels of Bcl-2 and Bcl-$X_L$, which regulate the release of cytochrome c from mitochondria, thus controlling apoptosome formation and activation of executioner caspases.

Cisplatin-based chemotherapy regimens cause progressive and persistent anemia, which is commonly attributed to renal tubular damage and subsequent decrease in serum Epo. However, some studies report a lack of correlation between serum Epo levels in patients treated with cisplatin or with other chemotherapeutics, raising the possibility that other mechanisms may contribute to cisplatin-induced erythroid suppression. We have observed a direct cytotoxic effect of cisplatin on erythroid precursors, which undergo caspase-mediated apoptosis following exposure to this drug. Because SCF seems particularly effective in preventing cisplatin-induced erythroblast apoptosis and promoting post-chemotherapy erythroblast recovery in vitro, it would be interesting to evaluate a possible use of this cytokine to ameliorate anemia caused by platinum-based therapies.

In conclusion, we provide evidence that SCF protects immature erythroid precursors from chemotherapy-induced apoptosis via upregulation of Bcl-2 and Bcl-$X_L$. While the clinical use of SCF for the prevention of chemotherapy-induced anemia in cancer patients may represent an interesting future possibility, further studies are required to understand the effects of SCF on the biology of neoplastic cells and to rule out the possibility of enhanced tumor cell growth after cytokine treatment.

Example 2

Decreased platelet number is a common side effect of chemotherapy. In a separate set of experiments, the protective effect of SCF on chemotherapy-induced cell death was evaluated on megakaryocytic cells, which derive from hematopoietic stem and progenitor cells and give rise to platelets. Purified hematopoietic progenitors grown in liquid suspension culture in the presence of thrombopoietin (TPO, used at 100 ng/mL) undergo a gradual wave of differentiation and maturation along the megakaryocytic lineage, giving rise to a virtually pure megakaryocytic population (98% to 99% of the cells are positive for the megakaryocytic marker CD61). The differentiation stages were characterized during the whole culture by morphologic and phenotypic analysis: at day 0, cells were essentially composed of small undifferentiated blasts; at day 6 most cells are larger than at day 0 and had one nuclear lobe, representing early megakaryocytic precursors. At day 12 most cells are multinucleated megakaryocytic precursors. After day 14, a significant production of platelets is observed. We treated day 6 and day 12 megakaryocytic precursors with chemotherapy (Etoposide 4 micromolar, or Daunorubicin 0.5 micromolar, or Vincristine 0.5 micromolar), and observe that day 6 immature precursors are the preferential target of chemotherapeutic drugs, as mature polynucleated megakaryocytic precursors are more resistant to the cytotoxic action of the chemotherapeutic agents tested (i.e. we observe 100% of death in early vs 20% of death in late megakaryocytic cells treated with Vincristine). We pretreated immature megakaryocytic precursors at day 4 of differentiation with SCF for 48 hours before exposure to chemotherapeutic agents. SCF was maintained during the exposure to chemotherapic agents. The concentration of SCF used in all the experiments was 100 ng/ml, as this dose has been shown to support maximal megakaryocytic cell survival in vitro. Cells treated with SCF and exposed to Etoposide, Daunorubicin or Vincristine were significantly protected from the toxic effects of antineoplastic drugs, even in conditions which do not allow the survival of any cells untreated with SCF, showing that SCF impairs the apoptotic program activated by chemotherapeutic agents in megakaryocytic cells. Moreover, after removal of chemotherapeutic drugs, those cells that have been treated with SCF are able to expand, differentiate and produce platelets. Thus, SCF protects megakaryocytic cells from chemotherapy and may be used alone or in combination with other cytokines or chemicals to prevent platelet depletion associated to cancer treatment.

The invention claimed is:

1. A method for reducing chemotherapy-induced depletion of thrombocytes, neutrophils or leukocytes in a human cancer patient, the method comprising:
   treating the cancer patient by administering an effective amount of a chemotherapeutic agent that is cytotoxic to cancer cells, which chemotherapeutic agent activates caspase in erythroblast cells;
   administering Stem Cell Factor to said patient before, for the duration of and after the administration of the chemotherapeutic agent, thereby reducing chemotherapy-induced depletion of thrombocytes, neutrophils or leukocytes in the patient.

2. A method as claimed in claim 1, wherein the Stem Cell Factor is administered in combination with another pharmaceutically active agent selected from the group consisting of Erythropoietin (Epo), interleukins from IL-1 to IL-23, granulocyte colony stimulating factor (G-CSF), granulocyte-macrophage colony stimulating factor (GM-CSF) and macrophage-colony stimulating factor (M-CSF), said pharmaceutically active agent being administered simultaneously, sequentially or separately with the Stem Cell Factor.

3. A method as claimed in claim 1, wherein said chemotherapeutic agent is one or more of Cisplatin, Camptothecin, Etoposide, Daunorubicin or Vincristine.

4. A method according to claim 3,
   wherein the Stem Cell Factor is administered in combination with another pharmaceutically active agent
   selected from the group consisting of Erythropoietin (Epo), interleukins from IL-1 to IL-23, granulocyte colony stimulating factor (G-CSF), granulocyte-macrophage colony stimulating factor (GM-CSF) and macrophage-colony stimulating factor (M-CSF),
   said pharmaceutically active agent being administered simultaneously, sequentially or separately with the Stem Cell Factor.

5. A method as claimed in claim 1, wherein the cancer patient is one having a solid tumor.

6. A method as claimed in claim 5, wherein the solid tumor is selected from the group consisting of lung cancer and gynecologic or genitourinary tumors.

7. A method as claimed in claim 2, wherein the cancer patient is one having a solid tumor.

8. A method as claimed in claim 7, wherein the solid tumor is selected from the group consisting of lung cancer and gynecologic or genitourinary tumors.

9. A method as claimed in claim 3, wherein the cancer patient is one having a solid tumor.

10. A method as claimed in claim 9, wherein the solid tumor is selected from the group consisting of lung cancer and gynecologic or genitourinary tumors.

11. A method as claimed in claim 4, wherein the cancer patient is one having a solid tumor.

12. A method as claimed in claim 11, wherein the solid tumor is selected from the group consisting of lung cancer and gynecologic or genitourinary tumors.

* * * * *